United States Patent [19]

Kimbell

[11] 4,127,780
[45] Nov. 28, 1978

[54] PERIODIC SAMPLING CONCENTRATION INDICATOR

[76] Inventor: Charles L. Kimbell, P.O. Box 40052, Houston, Tex. 77041

[21] Appl. No.: 682,374

[22] Filed: May 3, 1976

Related U.S. Application Data

[63] Continuation-in-part of Ser. No. 591,292, Jun. 30, 1975, abandoned.

[51] Int. Cl.² .................. G01J 1/44; G01R 19/12
[52] U.S. Cl. .................. 250/559; 73/432 CR; 250/214 RC; 250/564; 250/571; 307/152; 328/132; 356/448
[58] Field of Search ........... 250/559, 564, 571, 214 R, 250/214 RC; 356/70, 199; 328/132, 1, 2, 3; 307/308, 310, 311, 152; 73/15 B, 23, 23.1, 27 R, 432 CR

[56] References Cited

U.S. PATENT DOCUMENTS

| 3,596,190 | 7/1971 | Marshall | 328/132 X |
|---|---|---|---|
| 3,643,491 | 2/1972 | Dell et al. | 73/15 B |
| 3,869,666 | 3/1975 | Saltz et al. | 328/132 X |
| 3,872,728 | 3/1975 | Joyce et al. | 328/132 X |

Primary Examiner—Eugene R. LaRoche
Attorney, Agent, or Firm—Pravel, Wilson & Gambrell

[57] ABSTRACT

Apparatus for indicating the concentration of a particular constituent in a fluid including a sensing device for sensing the concentration of a particular constituent in a fluid and for providing a response; and an electronic device including a differentiating circuit for differentiating an electrical input signal which is proportional to the sensing response for providing a substantially constant output signal which is a measure of the sensing response differentiated with respect to time, which output signal is an indication of the concentration of the constituent in the fluid. The sensing device is operated during a sampling period in which the reaction of such constituent to the sensing device is linear.

28 Claims, 9 Drawing Figures

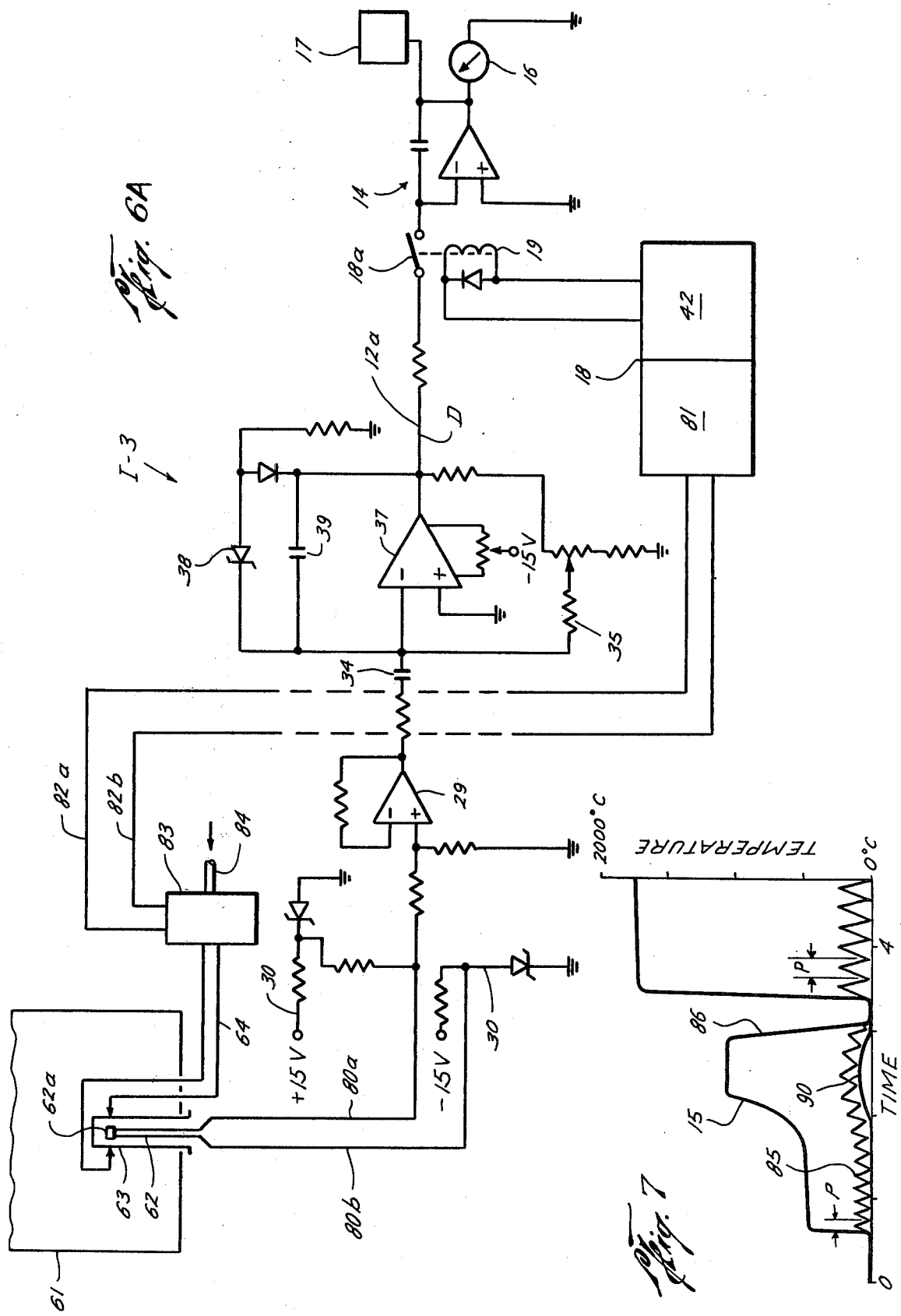

PERIODIC SAMPLING CONCENTRATION INDICATOR

CROSS-REFERENCE TO RELATED APPLICATIONS

This application is a continuation-in-part of U.S. patent application Ser. No. 591,292 filed on June 30, 1975, now abandoned.

BACKGROUND OF THE INVENTION

The field of this invention is the detection of a constituent in a fluid or of a condition in an atmosphere.

Undesirable and often dangerous gases such as carbon monoxide or hydrogen sulfide are often by-products of industrial plants such as oil refineries or chemical plants. These constituents should be detected quickly and accurately in order to prevent harm to workmen in the immediate area. Also, it is sometimes desirable to inject particular quantities of a constituent into a fluid, and the exact concentration must be accurately measured.

U.S. Pat. No. 3,464,799, invented by the inventor herein discloses a device for measuring the actual concentration of an undesirable constituent such as hydrogen sulfide in a gaseous medium. This device principally utilizes a chemical reaction type sensor—a paper strip impregnated with proper chemicals to provide discoloration upon reaction with a particular constituent in the gaseous medium. The paper strip is mounted on a reel in a substantially sealed housing such that only a particular portion of the tape is exposed to the atmosphere at any time. The discoloration on the tape is measured by an electrical circuit utilizing a light source directed against the area on the paper strip where the hydrogen sulfide has reacted; and, a measurement circuit reads the magnitude of the light reflected off of the paper strip and thus the magnitude of the concentration of the hydrogen sulfide on the strip.

Although the device of U.S. Pat. No. 3,464,799 has been found to be very reliable, it has been found necessary to improve upon this device in order to eliminate some problems inherent with attempting to measure the concentration of a particular constituent. For example, it is generally necessary to provide a continuing reference base in order to properly read concentration. Secondly an inherent limitation in measuring concentration has been that a considerable time has been required for equilibrium to be reached and a measurement obtained. Also, reversible reactions have been a problem where the chemical reaction of the constituent on the sensing material begins to reverse and thus fails to indicate the actual magnitude of the concentration of the constituent in the atmosphere. Another difficulty is the inherent background noise found in measuring an absolute such as magnitude of the reaction of the constituent on the sensing material.

SUMMARY OF THE INVENTION

It is an object of this invention to sense the change in the concentration of a particular constituent in a fluid and to convert the indication of the change into an electronic signal of substantially constant magnitude which is a measure of such rate of change, and thus a measure of the actual concentration of the constituent in the fluid.

It is further an object of this invention to measure the rate of change of concentration of a particular constituent in a fluid in order to reduce noise and to eliminate variations in the zero reference point.

It is further an object of this invention to measure the rate of reaction in order to obtain a reading during a period of linear reaction of the constituent with a sensing material to prevent the confusion caused by such non-linear reaction events as reaction reversing.

It is further an object of this invention to provide a system wherein periodic readings may be taken and samples may even be injected without having to wait for an equilibrium reaction to occur in order to measure the concentration.

This object and other objects of this invention are accomplished by the apparatus of the preferred embodiment of this invention for indicating the concentration of a constituent in a fluid by measuring the rate of effect of said constituent upon a sensing means.

The apparatus of this invention includes a sensing means for sensing a concentration of a particular constituent in a fluid and for providing a response proportional thereto. Further, electronic means detects and measures the response and provides an output signal indicative of the rate of change of the sensing means response. The electronic means includes signal conversion means for converting the response of the sensing means into a substantially constant output signal measuring the rate response which indicates the concentration of the constituent in the fluid.

The sensing means of this invention includes means for periodically exposing a constituent-sensitive material to such fluid, the constituent-sensitive material providing a response indicative of the effect of such constituent on the material with respect to time.

The electronic means of the preferred embodiment of this invention includes response detection means for detecting the changing response and for providing an electronic input signal proportional thereto. Differentiator means receive and differentiate the electronic input signal in order to provide a substantially constant output signal over a pre-designated period of time, the output signal being a measure of the rate response of the sensing means.

Signal display means are provided for receiving and sustaining the differentiated output signal over a predesignated period of time.

In one embodiment of this invention, the sensing means includes a semi-conductor type sensor which provides a changing resistance proportional to the amount of such constituent in such fluid with respect to time.

BRIEF DESCRIPTION OF THE DRAWINGS

FIGS. 6 and 6A are sectional and schematic views, respectively, of another preferred embodiment of the concentrator indicator apparatus of this invention utilizing a temperature sensitive thermocouple sensor to measure a condition such as temperature within a particular environment such as a furnace or the like; and, FIG. 7 is a display chart output illustrating an output display as based upon readings taken periodically within the environment such as a furnace.

DESCRIPTION OF THE PREFERRED EMBODIMENT

The concentration indicator apparatus I of the preferred embodiment of this invention is designed to provide an extremely accurate indicator of the concentration of a particular constituent in a fluid. For the purposes of describing the structure and operation of the concentration indicator I, the fluid will be presumed to be a gas and the constituent will be one of the compounds which may be present in the gas. For example, the constituent may be hydrogen sulfide or carbon monoxide or any other gaseous compound which would be dangerous to humans if present in sufficient quantities. It is within the scope of this invention to also analyze a constituent in a liquid. A constituent in a liquid may be analyzed by first practicing the invention disclosed in U.S. Pat. No. 3,756,781 issued to the inventor herein. In U.S. Pat. No. 3,756,781, a liquid hydrocarbon sample is first converted into a gaseous state and hydrogenator means react with the gas to convert sulfur in the gas into hydrogen sulfide which may be detected utilizing the concentration indicator I of this invention. The concentration of a constituent in a solid can also be measured by first pyrolizing the solid to a gas and utilizing the concentration indicator I of this invention. Thus it is within the scope of this invention to analyze a constituent which may initially be found in a gas such as air, or in a liquid such as a liquid hydrocarbon, or in a solid such as a plastic and the term fluid as used herein applies to all such circumstances.

Figure 1:
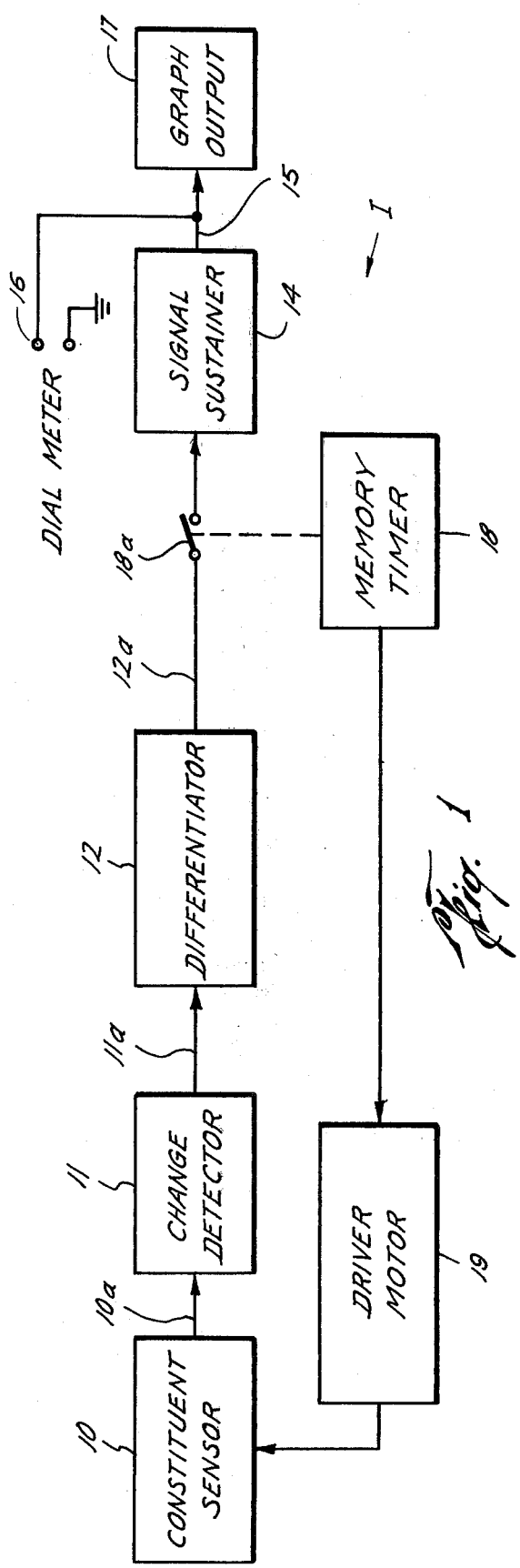
FIG. 1 is a block diagram of the concentration indicator apparatus of the preferred embodiment of this invention.
Figure 4:
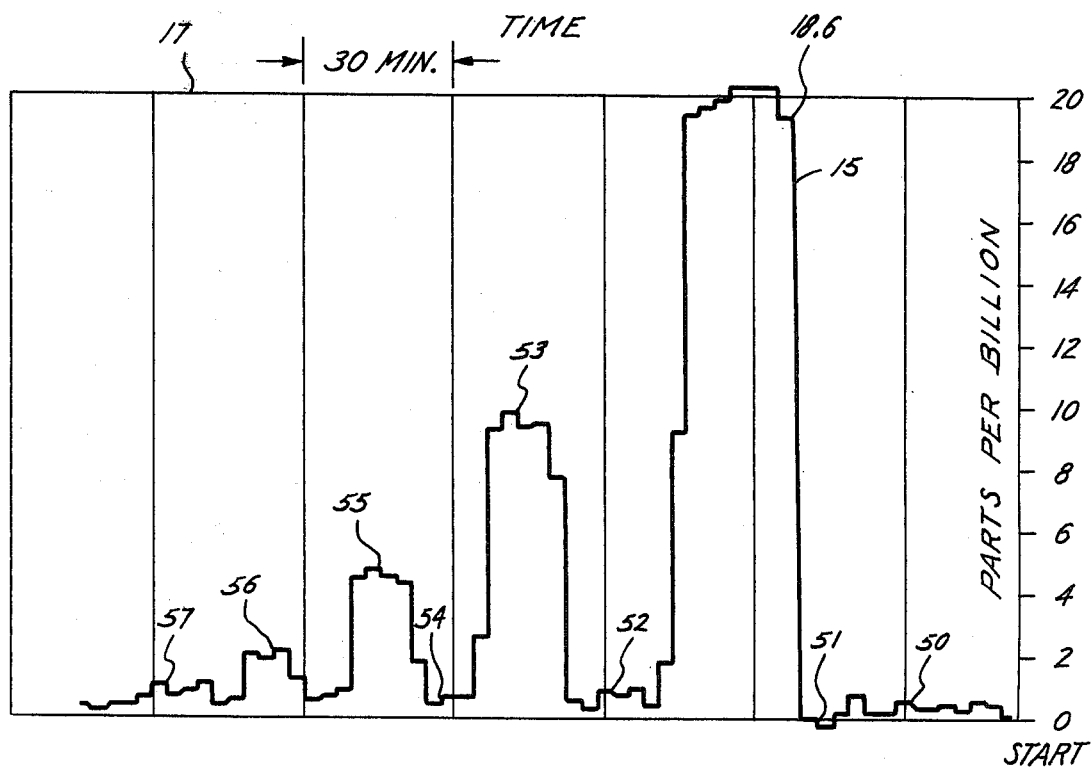
FIG. 4 is a sample of the display chart output provided by the display means, which includes a signal sustainer, utilized herein.

Referring in particular to FIG. 1, the concentration indicator I for determining the concentration of a constituent in a gas is illustrated in block diagram format. A constituent sensor 10 is periodically exposed to the gas medium being tested to provide a chemical reaction with the particular constituent in the gas which is of interest. The constituent sensor 10 provides a signal 10a which is proportional to the magnitude of this chemical reaction of the particular constituent with the constituent sensor. The signal 10a is detected by the response detector 11 which provides an electronic input signal 11a to a differentiator 12. The differentiator provides a differentiated signal 12a to a signal sustainer 14. The signal sustainer 14 receives and sustains an output signal 15 which indicates the concentration of the particular constituent in the gas sample being monitored. The output signal 15 is directed to a dial meter 16 and/or a graph output 17. An example of such a graph output 17 is illustrated in FIG. 4. The transfer of the differentiated signal 12a is controlled by switch 18a connected to the memory timer 18 by relay 19. The memory timer 18 also controls the driver motor 22 for the constituent sensor 10. The memory timer 18 acts to periodically operate the driver motor 19 in order to periodically prepare the constituent sensor 10 for a new reading of the rate of reaction of the constituent.

Figure 2:
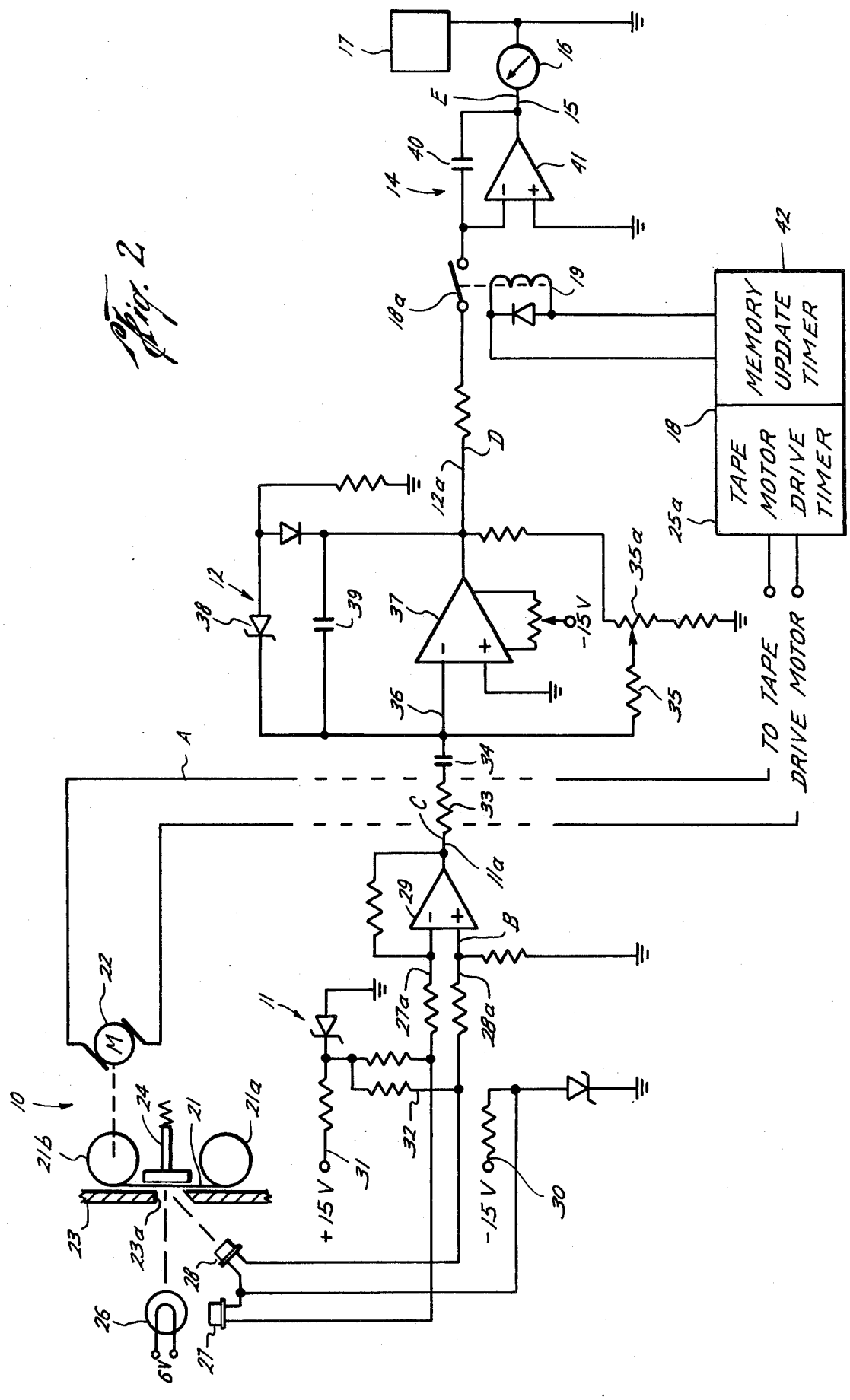
FIG. 2 illustrates the circuit detail of the electronic means for providing an output which is a measure of the rate of change of constituent in the fluid with respect to time.

In FIG. 2, the circuitry for the response detector 11, the differentiator 12 and the signal sustainer 14 is illustrated in detail. The constituent sensor 10 is basically identical to the constituent sensor illustrated in U.S. Pat. No. 3,464,799 of the inventor here. The constituent sensor includes a strip of constituent-sensitive material 21 mounted on reels 21a and 21b. The reels are controlled by a reel drive motor 22 which is mechanically connected to one of the reels such as 21b. The motor 22 positions the constituent-sensitive material 21 with respect to an opening 23a in the housing 23. The constituent-sensitive material 21 is positioned in a substantially sealed relationship with respect to the opening 23a in the housing by a spring-loaded backup bar 24. The motor 22 is electrically connected to the tape motor drive timer 25a which is part of the memory timer 18. The tape motor drive timer 25a periodically activates the motor 22 to rotate the reels 21a and 21b and thus move the material strip 21 such that a fresh portion is exposed through the opening 23a to the gas outside the housing 23.

A concentration light source 26 is positioned opposite from the opening 23a in order to direct a concentrated light beam at the material strip 21 aligned with the opening 23a.

In one embodiment of this invention, the material strip 21 is a lead acetate tape which chemically reacts with hydrogen sulfide in the gas, such as a flue gas, which is passing by the housing 23. The lead acetate and hydrogen sulfide chemically react and change color, which color is indicative of the amount of hydrogen sulfide which has reacted with the portion of the lead acetate tape exposed through the housing opening 23a. The lamp serves to illuminate the coloration on the lead acetate tape. Of course, it is within the scope of this invention to provide other types of constituent-sensitive materials and the use of the lead acetate tape to determine the presence of hydrogen sulfide is discussed here to provide a pertinent example only.

Dual photocells 27 and 28 provide part of the response detector circuit 11. The photocells 27 and 28 are of any suitable variety and provide input signals to the amplifier circuit 29. The photocell 27 is positioned to receive light directly from the light source 26 in order to provide a reference voltage input signal along line 27a. The photocell 28 is directed to receive light reflected off of the material strip 21 and provide a voltage along line 28a. These voltages are referenced by dc reference voltages at 30 and 31 and a bridge circuit generally designated by the number 32. The intensity of the signal from photocell 28 directed to the amplifier 29 is directly proportional to the color or shade of the reaction taking place on the material strip 21. The amplifier 29 amplifies the input signal to produce signal 11a which is conducted as a current signal through resistance 33 and directed to the differentiator capacitor 34 and differentiator resistor 35, which may be referenced to a resistor combination and ground generally designated as 35a.

The differentiator circuit formed by capacitor 34 and resistor 35 directs an output signal 36 to the amplifier 37. The initial differentiated signal 36 is clamped by the zener diode 38 which is connected in parallel with a low pass filter capacitor 39 in order to filter out at least some of the high frequency noise. The clamping diode 38 and the low pass filter circuit formed by capacitor 39 are well known in the art, as is the amplifier 37. The resultant differentiated output signal 12a is directed across switch 18a to the signal sustainer 14. The switch 18a is controlled through a solenoid 19 which is operated by a memory update timer 42 of memory timer 18 to periodically open and close in a timed relationship with respect to the activation of the motor 22 and the signal sustaining circuit 14. The differentiated output signal 12a is a measurement of the actual rate of reaction of the constituent with the strip of material 21.

The signal sustaining circuit 14 includes a signal sustaining capacitor 40 which receives the differentiated, amplified output signal 12a and, utilizing amplifier 41, directs an amplified, sustained signal to the meter 16 and the graph 17.

The memory update timer 42 illustrated in FIG. 2 and the tape motor drive timer 25a are both part of the memory timer which serves to control the tape motor 22 and the switch 18a in order to operate the concentration indicator I to take periodic readings of the rate of reaction of the constituent on the strip 21.

Figure 3:
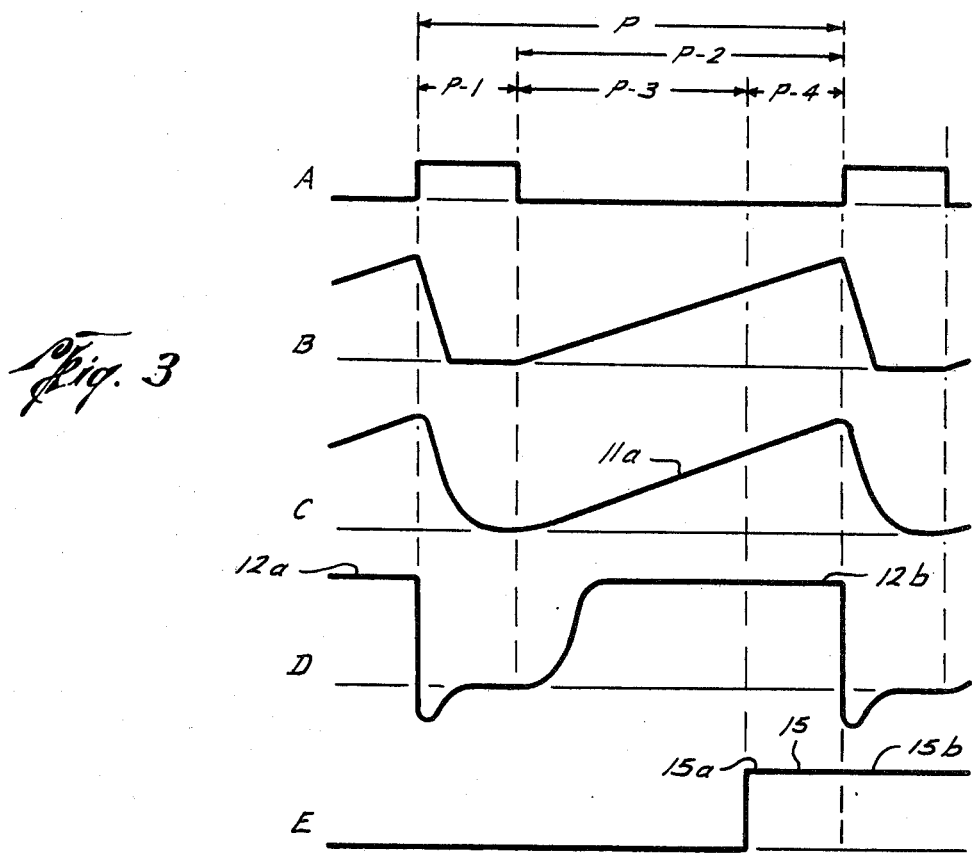
FIG. 3 is a series of voltage readings at various points in the electronic means of FIG. 2.

The timing control provided by the memory timer 18 may be best described with respect to the signal comparison made in FIG. 3. Referring to FIG. 3, the concentration indicator I is operated on a periodic basis in order to regularly determine the concentration of a constituent in the gas. The complete period is designated as P. This period may be any particular length of time which is necessary to obtain the proper rate of reaction indication on the material strip 21. Each period P may be broken down into two phases. The first phase P-1 is the motor run phase wherein the tape motor drive timer 25a activates the reel motor 22 to rotate the reels 21a and 21b and thus move a fresh strip of constituent-sensitive material 21 to a position aligned with the housing aperture 23a. The second phase is designated as P-2 and is a time span during which the particular constituent being sampled has a linear rate of reaction on the material strip 21. The phase P-2 may be sub-divided into a first phase portion P-3 during which the chemical reaction is building and a second phase portion P-4.

The second phase portion P-4 is actually the phase in which the switch 18a is closed by the memory update timer to obtain the rate of reaction reading. At the end of the phase portion P-4, the complete period P is repeated.

FIG. 3 further indicates the five most important signals which are utilized in the concentration indicator I of this invention. The five points at which these signals are taken have been designated by letters A-E in FIGS. 2 and 3.

The signal shown at reference point A indicates that energy is supplied to tape drive motor 22 during phase P-1 of the period P for exposing a fresh strip of material 21 by activation of the motor 22. This phase P-1 is repeated at the initiation of each period P.

The reading at B is the voltage input into the amplifier 29. It is noted that the reading is linear during the entire phase P-2. The slope of the line is a reading of the reaction taking place between the constituent and the material strip 21 within the housing aperture 23. This reaction is measured by the voltage level between the two photocells 27 and 28. The voltage level provided at B as an input to the amplifier 29 is proportional to the reaction of the constituent with the strip of material 21. One of the advantages of the utilization of the rate of reaction is that a linear, non-reversible portion of the reaction on the material strip by the constituent can be measured. Therefore, it is not necessary to take into consideration in any way whether or not a reaction is reversible so long as the period of time designated provides an accurate indication of the rate of reaction. The rate of reaction is proportional and indicative of the actual concentration of the constituent in that the greater the amount of concentration of the constituent, the greater the rate of reaction. The reading at C is a reading of the amplified output from the detection means 11 and the signal itself has been designated at 11a. Capacitor 34 and resistor 35 differentiate the signal providing a signal measure to the rate of reaction. This rate signal is proportional to the concentration of the constituent.

The reading at D is the amplified, differentiated output signal 12a. The level or flat portion 12b is the differentiation of the sloped portion of the signal 11a and thus is a measure of the rate of reaction of the constituent on the material strip with respect to time.

The memory update timer 42 of the memory timer 18 acts to close the switch 18a during phase portion P-4 of the phase P-2. The switch 18a is opened at the end of the phase P-4 and the motor run phase P-1 is again initiated. Thus the differentiated signal passes to the signal sustaining circuit 14 only during the phase P-4. Referring to the reading at point E, the first portion of the stepped output 15a is provided directly by the amplification of the signal 12a. The second portion 15b of the output signal 15 is actually provided by the sustaining capacitor 40 as amplified by the amplifier 41. The signal sustaining capacitor 40 acts to sustain the signal at 15a for a period of time equal to the sum of the phase portions P-1 plus P-3. In this manner, a constant output signal 15 is provided for a time span equal to a complete period P. Of course, a new output signal 15 is initiated at each phase portion P-4, but this output signal 15 is provided for a complete period so that to the user, an output signal 15 is constant until a new output signal is received.

EXAMPLE

FIG. 4 is an example of a graph which has been provided of the output signal 15 utilizing one of the embodiments of this invention. In FIG. 4, the graph 17 is an indication of readings obtained wherein a strip of lead acetate 21 was exposed to a gas sample having the constituent hydrogen sulfide. In this example, the period P is three minutes such that the time span thirty minutes indicates a series of ten successive readings on the graph 17. The ordinate is marked zero to twenty to indicate the number of parts per billion of hydrogen sulfide in normal air.

Initially, the readings are along a level at 50 around zero and are simply clean air. However, at point 51, hydrogen sulfide has been injected into the gas being sampled in a relatively large quantity such that one period P later a reading of 18.6 parts per billion is indicated on the graph. This reading level around 18.6 parts per billion continues for a certain time frame and then fresh air is injected into the system to cause the reading to go back down to about zero at 52. The readings obtained are actually rate of reaction readings and should be read with respect to time. For example, the 18.6 parts per billion should be read with respect to a time period equal to P-4. Thus the entire group of readings at the level of about 18.6 parts per billion indicates that a rather significant amount of hydrogen sulfide is being injected into the system at the rate of approximately 18.6 parts per billion per period of time equal to P-4.

After the air has been cleaned, which is indicated by the reading at 52, another hydrogen sulfide sample is passed by the indicator I. However, this time the strength of the sample is only half of the strength previously and the readings at 53 are thus only approximately half of the rate of reaction readings at the 18.6 reading. Fresh air is again injected and fresh air readings are found again at 54. Thereafter, a sample is injected into the system which is one-quarter of the concentration of the original sample and thus the readings at 55 are approximately one-quarter of those of the initial sample. This process is repeated at 56 for readings at one-tenth of the initial injection and at 57 for readings at one-twentieth. It is thus seen that there is a direct correlation between the actual concentration in the sample and the rate of reaction of the sample with the strip of material. On this basis, the readings indicating the rate of reaction are a proportional indicator of the concentration of the constituent such as hydrogen sulfide in air.

Figure 5:
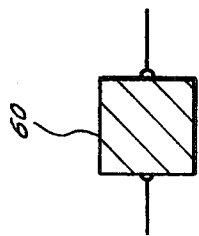
FIGS. 5 and 5A are cross-sectional and schematic operational diagrams of a concentration indicator apparatus of another embodiment of this invention utilizing a semi-conductor type sensor.
Figure 5A:
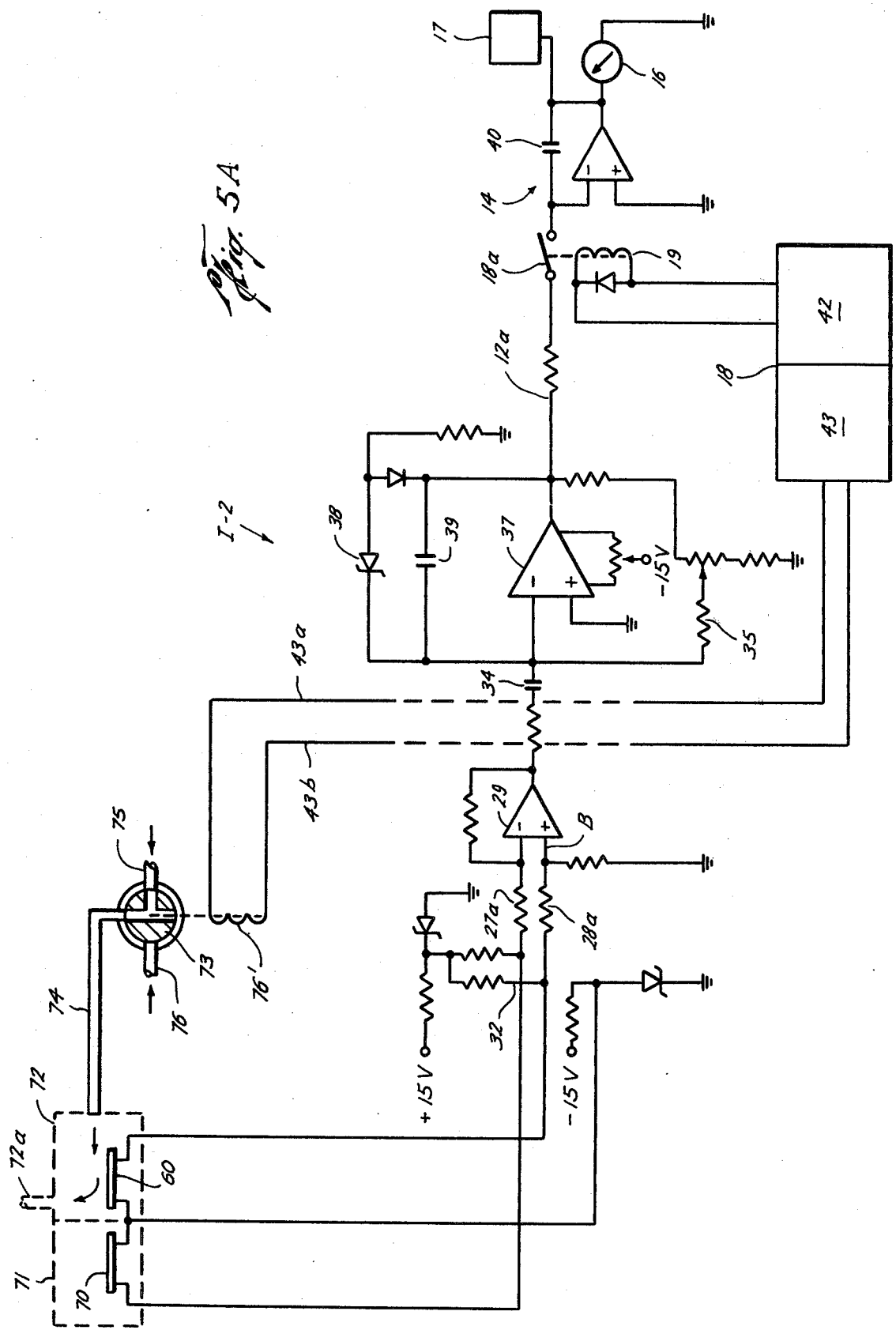

It is within the scope of this invention to utilize other constituent sensors 10 than the chemically reactive strip of material such as 21. Referring to FIGS. 5 and 5A, another embodiment I-2 of the concentration indicator is illustrated. In the embodiment shown in FIGS. 5 and 5A, a semi-conductor type sensor 60 is utilized to sense a particular constituent in a fluid. The semi-conductor 60 is utilized in an electronic circuit system which is very similar to the electronic circuit system for the concentration indicator I of FIGS. 1 and 2. Therefore, the same numbers and letters will be utilized wherever possible to identify the same parts.

The semi-conductor sensor 60 is attached through suitable electric lines in parallel to a reference semi-conductor 70. The semi-conductors 60 and 70 are connected to the bridge circuit 32 which provides a desired reference voltage to input lines 27a and 28a of the amplifier circuit 29. The reference semi-conductor 70 is housed in a sealed housing 71 which contains a reference fluid. For example, if the unit I-2 is utilized to provide readings of the presence of hydrogen sulfide in air, fresh clean air will be sealed into the housing or container 71 so that a constant, clean reference voltage 70 may be provided. The semi-conductor 60 is mounted in a housing 72 of any suitable nature to receive a stream or flow of the fluid being tested for the particular constituent in question. A three-way valve 73 is attached to a line 74 which is mounted in the housing 72. An exit line 72a is also illustrated for the housing 72. The three-way valve 73 has the well-known three-way type of internal passage for selectively connecting a fresh air line 75 or a sample air line 76 into line 74. The three-way valve 73 is operated by a solenoid 76 mechanically connected therewith.

The remainder of the electrical circuit for the unit I-2 is basically identical to that for the unit I. Differentiator capacitor 34 and resistor 35 again receive the input signal from amplifier 29 and differentiates said signal, which is then received by amplifier 37 as clamped by dial 38 and filtered by capacitor 39. The resultant differentiated output signal 12a passes to signal sustainer 14 only when switch 18a is closed. Switch 18a is closed by solenoid 19 by the memory timer 18 and in particular memory update timer component 42. The signal passing through switch 18a is sustained by signal sustaining capacitor 40 for reporting on a meter 16 or graph output 17.

A memory update timer 42 is operably connected to a solenoid actuator circuit of any well-known variety and designated by the number 43. The solenoid actuator 43 is connected by lines 43a and 43b to the solenoid 76 in order to selectively operate the three-way valve 73.

The concentration indicator apparatus I-2 is operated in the following manner. In describing the operation, reference will be made to the phases as previously defined in FIG. 3, the same basic principles applying.

The concentration indicator I-2 is operated on a total period P. During the initial part of the total period P, which is defined as period or phase P-1, the solenoid actuator 43 operates the solenoid 76 to direct a flow of fresh air from line 75 into line 74 and thus into the housing 72 for the sensor 60. This fresh air returns the semi-conductor element 60 to an initial condition wherein the resistance of the conductor is at a value indicative of zero presence of the constituent being tested.

At the end of the re-set phase P-1, the solenoid actuator 43 actuates solenoid 76 to cause valve 73 to connect sample air or other fluid line 76 to the line 74 so that sample air is directed into the housing 72 to affect the semi-conductor element 60, which may be a metal oxide element or other similar element. The sample air is injected through line 74 for sampling period P-3. At the end of sampling period P-3, solenoid actuator 43 is actuated to cause three-way valve 73 to again connect fresh air line 75 to the line 74 in order to revert the semi-conductor element 60 to its initial condition again.

During the sampling period P-3, the resistance of the semi-conductor element 60 varys according to the amount of the particular constituent being tested present in the sample being passed through the housing 72. The resistance 60 will increase at a rate depending upon the actual concentration of the constituent being tested in the sample. The reference voltages will cause a voltage reading proportional to this change in resistance similar to that illustrated at B in FIG. 3. The input signal is passed through the amplifier 29 and then differentiated continuously during the sample period. During the last part of the sample period, a phase or period designated as P-4, a readout is provided by closing switch 18a. This readout is of the differentiated input signal as amplified by amplifier 37. The memory update timer 42 only closes switch 18a for the readout period P-4. At the end of the readout period P-4, the switch 18a is again opened and the solenoid actuator 43 acts to cause three-way valve to connect reference or fresh air line 75 with line 74 in order to revert the semi-conductor element sensor 60 to its initial condition. In the meantime, the signal sustaining circuit 40 continues the signal passed through switch 18a for a period of time equal to phases P-1 plus P-3 so that the actual signal passed to meter 16 and graph 17a continues for the total period P. This process is continually repeated. It is noted that the choice of the sampling period P-3 to provide a linear input signal of increasing slope is very important to the system. Further, the choice of the readout period P-4 prior to any change in the slope, during the actual linear increase in voltage, is also very important.

Figure 6:
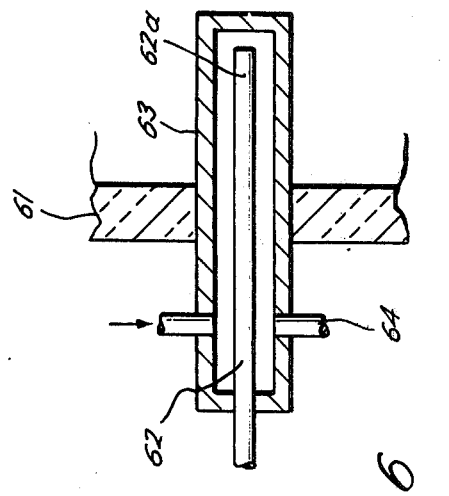

Referring to FIGS. 6 and 6A, a condition-indicator apparatus I-3 is illustrated for determining a condition such as temperature in an environment such as a furnace. In FIG. 6A, a furnace wall 61 is schematically illustrated. A casing 63 is mounted within the furnace wall 61 to house a sensing element 62. In the embodiment illustrated, the sensing element 62 is a thermocouple which is positioned within the casing 63 such that thermocouple end 62a is exposed to the furnace environment. It is well-known that thermocouples respond to temperature with a change in generated voltage output. However, in very high temperature areas or environments such as furnaces, thermocouples are very difficult to utilize because the elements tend to melt when heated to the actual temperature within the furnace. The utilization of a thermocouple sensor 62 in combination with the electronic circuitry of the unit I-2, which is basically similar to the units I and I-1, provides a unit which can repeatedly and periodically measure the actual temperature within the furnace wall 61 without destroying the thermocouple sensor 62. Since the condition indicator apparatus I-3 of FIGS. 6 and 6A is basically identical to the units I and I-1, the same numbers and letter designations will be used wherever possible to describe the same parts.

The thermocouple 62 is connected by lines 80a and 80b to dc reference voltages 30 and 31. Line 80a is connected to amplifier 29 such that the output generated from the thermocouple 62 is amplified prior to differentiation by the combination of capacitor 34 and resistor 35. The differentiated signal is again amplified at 37. The output signal of amplifier 37, which is suitably filtered by capacitor 39 and clamped by diode 38, is conducted through switch 18a when the switch is closed. When the output signal of amplifier 37 is directed through switch 18a, such signal is sustained by the signal sustaining circuit 14 which has been previously described in detail. The sustained output is passed to display elements 16 and 17. The switch 18a is controlled by the memory timer 18, which includes memory update timer 42 and valve actuator circuit 81. The valve actuator circuit 81 may be made of any suitable well-known elements which are capable of passing electrical signals, upon actuation by memory update timer 42, through lines 82a and 82b to an electrically actuated valve 83. The electrically actuated valve 83 controls the passage of a fluid coolant through line 84 to the line 64 connected to the thermocouple casing 63.

The line 84 may be connected to any suitable source of coolant. Such coolant may be water or any other fluid, gas or liquid, which is capable of reducing the temperature of the thermocouple back to an initial condition.

The operation of the condition indicator I-3 may be described in relation to FIG. 3. Reference will also be made to FIG. 7 which is an indication of an exemplary graph output from utilization of the unit I-2. The entire operating period which is continually repeated is again defined as P. The first portion or phase P-1 is the phase in which the thermocouple 62 is initially set or reverted to an initial temperature level. This is accomplished by the memory update timer 42 activating the valve actuator circuit 81, which opens valve 83 to allow coolant to flow to lines 64 into the casing 63. At the end of phase P-1, the valve actuator circuit 81 acts to close valve 83. The length of phase P-1 and the temperature of the coolant 84 has been pre-designated in order that the thermocouple 62 will be cooled to a pre-designated initial temperature.

The sampling period or phase P-3 then begins. During this phase, the thermocouple 62 is exposed to the heat within the furnance walls 61. The difference in temperature between the initial temperature of the thermocouple 62 and the actual temperature in the furnace, which is, of course, much higher, will cause the temperature of the thermocouple to gradually increase. As the temperature of the thermocouple increases, a current is generated in line 80 and is applied as an input signal to amplifier 29. The amount of the current will be dependent upon the temperature of the thermocouple 62 and, the temperature of the thermocouple 62 will be dependent upon the difference in temperature between the initial temperature of the thermocouple 62 and the actual temperature in the furnace. Therefore, the greater the actual temperature in the furnace, the greater the rate of increase of temperature of the thermocouple 62 over the sampling period P-2. The gradually increasing electrical input signal through line 80a is amplified by amplifier 29 and then differentiated prior to being again amplified at 37. The output signal 12a at point D is passed through switch 18a to signal sustaining circuit 14 whenever the switch 18a is closed. Memory update timer 42 operates solenoid 19 to close the switch 18a during phase P-4 of the sampling phase P-2.

The memory update timer 42 acts to open the switch 18a at the end of phase P-4. At that point, phase P-1 begins again with the memory update timer 42 actuating the valve actuator circuit 81 to open valve 83 and again cool the thermocouple 62. Without this periodic cycle of cooling and heating, the thermocouple 62 could not be effectively utilized because it would approach the temperature of the furnace and become ineffective. The signal sustaining circuit 14 sustains the signal generated and passed through switch 18a during period P-4 for an additional period or phase equal to phase P-1 plus phase P-3 so that the differentiated output signal is sustained for a period actually equal to the period P. Whenever switch 18a is opened for a new signal at the beginning of the next phase P-4, the signal output to the display elements 16 and 17 is changed and the signal sustaining circuit 14 then sustains that signal. This process is repeated continually over the total period P.

FIG. 7 is a graph illustrating an output signal 15. It is noted that the output signal 15 is substantially continuous. The sawtooth curve 85 actually represents the temperature of the thermocouple or the input signal derived from the thermocouple 62. The period P of a reading actually extends from peak to peak or valley to valley of the sawtooth curve 85. During such period P, the sampling period P-2 occurs during the increasing slope portion of each sawtooth and the re-setting period P-1 occurs during each declining slope portion of each saw tooth. The signal sustaining circuit provides the smooth differentiated output signal 15. It is noted that the signal dips significantly to zero degrees centigrade at area 86. The purpose of this is simply to illustrate the furnace being cooled to zero degrees centigrade and then heated back up again and how such cooling off and heating of the furnace itself would appear on the final output display.

One of the problems with long-term operation of some types of sensors such as thermocouples is a permanent drift in base line value. This is represented by the line 90, which illustrates in FIG. 7 a short-term drift. If absolute reading methods of the prior art devices are used, such changes in base line values (initial condition values) will cause a change in the absolute values of sensor response. However, utilization of the differentiator circuit of this invention eliminates such misleading effects. For use of the invention of I-3 allows for accurate readings to be taken from the more reliable slope of the curve and thus eliminates any reliance on absolute values.

It is thus within the scope of this invention to provide various types of constituent or condition sensors such as sensors 10, 60 or 62. Such sensors provide a signal response which is proportional to the actual constituent or condition present in the fluid or environment being tested. This response is then differentiated over a sampling period in which the initial input signal from the sensor is entirely linear. The time periods involved are all predesignated such that the reading occurs over a period of increasing slope only prior to any peak and slope decline. It is important and critical to this invention that such reading occur during a sampling period in which the initial input signal is increasing and linear only.

Another application is a gas sampling instrument such as a gas chromatograph which produces a series of elution peaks (on a mechanical graph) which indicate the concentration of several different gases. Difficulties are encountered in determining the actual concentration of each gas because the chromatograph response peaks are produced in a very rapid succession. The indicator I can be used to first detect, by a suitable sensor means such as the strip material sensor 21, and then by causing differentiator 12 to provide an output signal, produce a better resolution indicative gas concentration simply by shortening the time period P of operation of I.

The foregoing disclosure and description of the invention are illustrative and explanatory thereof, and various changes in the size, shape and materials as well as in the details of the illustrated construction may be made without departing from the spirit of the invention.

I claim:

1. Apparatus for indicating the concentration of a constituent in a fluid, comprising:
    sensing means for sensing the concentration of a particular constituent in a fluid and providing a linear response indicative of said concentration;
    time control means for periodically activating said sensing means for a predesignated sampling phase in which said response is linear, said sensing means providing said linear response over said predesignated sampling period;
    input signal means for reading said linear response over said sampling phase and for providing an input signal for said sampling phase indicative of said linear response;
    signal conversion means for converting said input signal for said sampling phase into a substantially constant output signal indicative of the rate of said linear response of said sensing means over said sampling phase such that said output signal is indicative of the concentration of such particular constituent in said fluid; and
    display means for reporting said output signal.

2. The structure set forth in claim 1, including:
    said signal conversion means includes differentiator means for differentiating said linear response and providing a differentiated signal measuring the rate of change of said response.

3. The structure set forth in claim 1, wherein said display means includes:
    means for sustaining said output signal until a new output signal is received from said signal conversion means.

4. The structure set forth in claim 1, wherein said sensing means includes:
    a constituent-sensitive material; and
    exposure means periodically exposing said constituent-sensitive material to said fluid, said constituent-sensitive material providing a linear response indicative of the effect of such constituent on said constituent-sensitive material.

5. The structure set forth in claim 4, wherein said input signal means includes:
    response detection means for detecting said linear response and providing an electronic input signal proportional thereto, said linear response detection means detecting said response over said predesignated sampling phase in which the effect of said constituent on said constituent-sensitive material is linear.

6. The structure set forth in claim 5, wherein said signal conversion means includes:
    differentiator means for receiving said electronic input signal and differentiating same to provide a differentiated output signal that is a measure of the linear rate of response of constituent-sensitive material to such constituent.

7. The structure set forth in claim 6, wherein said display means further includes:
    means for receiving, sustaining and displaying said differentiated signal on a graph until a new differentiated signal is received.

8. The structure set forth in claim 1, including:
    said display means includes means for reporting said output signal during a time in which said input signal is increasing in intensity.

9. The structure set forth in claim 1, wherein said display means includes:
    means for reporting said output signal during a read-out phase which is a portion of said sampling phase.

10. The structure set forth in claim 1, wherein:
    said time control means includes means operably connected to said sensing means for operating said apparatus on a repetitious predesignated total time period which includes said sampling phase; and
    said time control means connected to said display means including means for activating said display means periodically during a read-out of said sampling phase.

11. The structure set forth in claim 10, including:
    said time control means including means for re-setting said sensing means during a re-set phase of said total period occurring in each total period at the end of said sampling phase.

12. The structure set forth in claim 10, including:
    said display means including means for sustaining said output signal for a predesignated time period.

13. The structure set forth in claim 1, including:
    said sensing means includes a strip of material which is chemically reactive with said constituent, said material varying in color with the stage of the reaction; and
    said input signal means including detector means for providing an electronic input signal proportional to the change in color of said material; and
    said signal conversion means including differentiator means for differentiating said input signal and providing an output signal measuring the rate of reaction.

14. The structure set forth in claim 1, wherein said sensing means includes:
    a semi-conductor type of sensing means providing a resistance proportional to the amount of constituent in said fluid; and
    said input signal means including detector means connected with said semi-conductor type of sensing means for providing an electrical signal proportional to said resistance of said semi-conductor type of sensing means.

15. The structure set forth in claim 14, including:
said time control means including means for periodically activating said semi-conductor type of sensor means including means for periodically exposing said semi-conductor type of sensor means to a clean reference fluid to return said resistance to an initial level prior to each sampling phase.

16. The structure set forth in claim 15, wherein said fluid is air, including:
said clean reference fluid being air without such constituent to be detected.

17. The structure set forth in claim 14, wherein said semi-conductor type of sensing means includes:
first and second semi-conductor elements;
first enclosure means for positioning said first semi-conductor element in such fluid to be tested; and
second enclosure means for sealing said second semi-conductor means in a chamber of reference fluid having a predesignated amount of such constituent so that a permanent reference point is utilized.

18. The structure set forth in claim 1, wherein:
said sensing means is at an initial condition at the beginning of said sampling period, said sensing means being unaffected by such constituent in said initial condition; and
said time control means including means for periodically recreating said initial condition in said sensor means after each sampling phase.

19. Apparatus for indicating the presence of a condition in an environment, comprising:
sensing means for sensing a particular condition in an environment and providing a linear response indicative of said condition;
time control means for periodically activating said sensing means for a predesignated sampling phase, said sensing means providing said response over said predesignated sampling phase in which said response is linear;
input signal means reading said linear response over said sampling phase and providing an input signal indicative of said response;
signal conversion means for converting said input signal for said sampling phase into a substantially constant output signal indicative of the linear rate of response of said sensing means over said sampling phase such that said output signal is indicative of the degree of presence of a particular condition in an environment; and
display means for reporting said output signal to a display.

20. The structure set forth in claim 19, wherein said display means includes:
means for reporting said output signal during a read-out phase, said read-out phase being a portion of said sampling phase.

21. The structure set forth in claim 20, including:
said condition being measured is temperature and said sensing means being a temperature-sensing element; and
said time control means including means for periodically exposing said temperature-sensitive element to said environment.

22. The structure set forth in claim 21, including:
said time control means including means for returning said temperature-sensitive element to its initial temperature at the beginning of said sampling phase.

23. The structure set forth in claim 21, including:
said time control means including means for cooling said temperature-sensitive element sufficiently below the anticipated temperature in such environment that the temperature-sensitive element will provide a linear, increasing response which is indicative of the actual temperature in said environment.

24. The structure set forth in claim 20, wherein:
said time control means includes means operably connected to said sensing means and to said input signal means for operating said apparatus over a repetitious predesignated total time period which includes said sampling phase; and
said time control means being operably connected to said display means and including means for activating said display means periodically during a read-out portion of said sampling phase.

25. The structure set forth in claim 20, including:
said time control means including means for re-setting said sensing means during a re-set portion of said total period, said re-set portion occurring in each total period at the end of said sampling phase.

26. The structure set forth in claim 20, including:
said signal conversion means including differentiator means for differentiating said input signal and providing a differentiated signal measuring the rate of change of said input signal over said sampling phase.

27. A method of analyzing a condition in an environment, comprising the steps of:
providing a sensing device for sensing a particular condition in an environment;
operating said sensing device over a sampling phase in which the response of said sensing device is entirely linear and of increasing intensity;
inputting said response into an electronic circuit in the form of an electronic input signal and differentiating such input signal to provide a substantially constant output which is indicative of the condition in said environment; and
displaying said output for another predesignated period.

28. A method of analyzing the concentration of a constituent in the fluid, comprising the steps of:
providing a sensing device for sensing the concentration of a particular constituent in a fluid and positioning said sensing device in fluid communication with said fluid;
operating said sensing device over a sampling phase in which the response of said sensing device is entirely linear and of increasing intensity;
inputting said response into an electronic circuit in the form of an electronic input signal and differentiating such input signal to provide a substantially constant output which is indicative of a concentration of the particular constituent in the fluid; and
displaying said output for another predesignated period.

* * * * *